United States Patent
Choi et al.

(10) Patent No.: US 6,981,873 B2
(45) Date of Patent: Jan. 3, 2006

(54) DENTAL IMPLANT AND HEAD FOR A COMPACTION DRILL

(76) Inventors: Young-Wook Choi, 106-1101 Sindonga Apt., 22, Nonhyeon-dong, Gangnam-gu, Seoul (KR), 135-010; Yong-Chang Choi, 23-907 Misung Apt., 408, Apgujeong-dong, Gangnam-gu, Seoul (KR), 135-110; Shin-Koo Kim, 103-706 Hansin Apt., 609-1, Donam-dong, Seongbuk-gu, Seoul (KR), 136-060; Han-Gu Kim, 534-301 Samsung, Hwajeong-dong, Deokyang-gu, Goyang-si, Gyeonggi-do (KR), 412-270; Jai-Hyun Lee, 228-506 Mokdong Sinsigaji, Mok-dong, Yangcheon-gu, Seoul (KR), 158-050

( * ) Notice: Subject to any disclaimer, the term of this patent is extended or adjusted under 35 U.S.C. 154(b) by 67 days.

(21) Appl. No.: 10/432,627

(22) PCT Filed: Nov. 14, 2001

(86) PCT No.: PCT/KR01/01936

§ 371 (c)(1),
(2), (4) Date: Jun. 6, 2003

(87) PCT Pub. No.: WO02/45615

PCT Pub. Date: Jun. 13, 2002

(65) Prior Publication Data

US 2004/0219488 A1 Nov. 4, 2004

(30) Foreign Application Priority Data

Dec. 9, 2000 (KR) .............................. 10-2000-0074878

(51) Int. Cl.
*A61C 8/00* (2006.01)

(52) U.S. Cl. ..................................... 433/173; 433/174

(58) Field of Classification Search ................. 433/172, 433/173, 174, 175, 176

See application file for complete search history.

(56) References Cited

U.S. PATENT DOCUMENTS

| | | | |
|---|---|---|---|
| 4,998,881 A | | 3/1991 | Lauks ......................... 433/173 |
| 5,205,745 A | * | 4/1993 | Kamiya et al. ............. 433/173 |
| 5,588,838 A | | 12/1996 | Hansson et al. ............ 433/173 |
| 5,702,346 A | | 12/1997 | Lazzara et al. |
| 5,727,943 A | | 3/1998 | Beaty et al. |
| 5,816,809 A | * | 10/1998 | Sapkos ........................ 433/172 |
| 5,816,812 A | | 10/1998 | Kownacki et al. .......... 433/173 |
| 5,897,320 A | * | 4/1999 | Gittleman ................... 433/180 |
| 5,967,783 A | * | 10/1999 | Ura ............................. 433/174 |
| 5,997,299 A | | 12/1999 | Unger |
| 6,095,817 A | * | 8/2000 | Wagner et al. .............. 433/173 |
| 6,227,857 B1 | * | 5/2001 | Morgan et al. ............. 433/173 |
| 6,325,628 B1 | * | 12/2001 | Morgan ....................... 433/173 |
| 6,527,554 B2 | * | 3/2003 | Hurson et al. .............. 433/173 |
| 6,547,564 B1 | * | 4/2003 | Hansson ..................... 433/174 |

* cited by examiner

*Primary Examiner*—Cary E. O'Connor
(74) *Attorney, Agent, or Firm*—Greenblum & Bernstein, P.L.C.

(57) ABSTRACT

A dental implant includes a fixture and an abutment in a body, and a head for a compaction drill is configured for implanting such an implant. The implant includes an upper abutment portion on which a denture is fixed, a fixture portion implanted in the jawbone and forming single or double threads, and a settling portion formed between the abutment portion and the fixture portion. The invention improves the stability of the implant, improves stabilization of the bone tissue affixed to the implant, effectively seals the socket from its surroundings and facilitates bonding between implant and jawbone. This is achieved because of the early healing of tissue around the implant and the greater surface area in contact with surrounding tissue. As a result, an artificial crown may be coupled with the implant during the same surgery.

16 Claims, 16 Drawing Sheets

DENTAL IMPLANT AND HEAD FOR A COMPACTION DRILL

TECHNICAL FIELD

The present invention relates to a dental implant and a head for a compaction drill, and more particularly to a dental implant that can immediately brace artificial dental structures thereon after the implant is placed because the implant includes a fixture and an abutment in a body can be easily implanted in a jawbone by an improved structure of the fixture, and also can accomplish enhanced bonding between a bone tissue and the implant. The present invention also relates to a head for a compaction drill specially designed for the implant.

BACKGROUND ART

In general, a dental implant is used as an artificial root composed of a metal having the shape of the crown root implanted in the jawbone where teeth are totally or partially lost so as to form artificial crowns on the artificial root after the artificial root combined with the jawbone. Such dental implants are available in varieties requiring two separate surgeries as well as varieties requiring only one.

Currently, those varieties requiring only one surgery have the aesthetic disadvantage that the metal portion of the implant is exposed above the gum line. This disadvantage does not apply in the case of those varieties requiring two surgeries, however, the inconvenience and expense of an extra surgery are disadvantages in themselves.

Dental implants can be classified according to the location of the implant such as "sub-periosteal" (beneath the periosteum), "intra-osseous" (within the connective tissue), etc. Implants can also be classified according to their shapes such as threaded implant, cylindrical implant, etc. These implants will not damage adjacent teeth, they prevent osteolysis in the gum, and they generally allow for a functionally and aesthetically adequate restoration that won't become dislodged by talking, laughing or eating. As a result of the above merits, such implants have become increasingly popular among dental patients. Such implant is disclosed at U.S. Pat. No. 5,727,943 issued to Beaty et al., entitled "SELF-TAPPING, SCREW-TYPE DENTAL IMPLANT".

FIG. 1 is an exploded perspective view for showing the conventional implant and FIG. 2 is a projected perspective view for explaining the conditions under which an artificial tooth is placed on the implant such as is shown in FIG. 1.

Referring to FIG. 1 and FIG. 2, the implant 10 includes an artificial root 20, a connection column 30 and an artificial crown 40.

The artificial root 20 is referred to as a "fixture" and fulfills the same role as the root of a natural tooth. It is implanted into the jawbone 45 where teeth are missing. The artificial root 20 supports the whole implant including the connection column 30, which connects the artificial root 20 to the artificial crown 40.

The connection column, referred to as an "abutment", is connected to the artificial crown 40, which is fixed in the gums above the jawbone. The upper part of the connection column 30 contains a screw hole corresponding to a screw 55 that holds the artificial crown 40 in place. On the lower portion of the connection column, the screw 55 is inserted into a locking hole 65 formed vertically through the artificial root 20. A projecting portion 70 is formed on the upper portion of the connection-column screw 55 and connected to the artificial crown 40.

In order to secure the artificial crown 40 to the artificial root 20 using the connection column 30, the implant further comprises a cone-shaped hole 75, formed in the under surface of the artificial crown 40, and threaded gold cylinder 80, extending up through the artificial crown 40. A hole 95 is formed all the way through the artificial crown 40 from above. The artificial crown 40 is mounted on the gold cylinder 80, and is fixed to the artificial root 20 by the connection column 30 using the threaded projection portion 70 and a gold screw 90 implanted through the tooth hole 95. The artificial crown 40 is secured in the mouth on the connection column 30, replacing the natural tooth.

FIG. 3 is an enlarged sectional view for illustrating the artificial root 20 implanted into the jawbone 45 in FIG. 2. FIG. 4 is an enlarged bottom view for showing the bottom of the artificial root 20 implanted into the jawbone 45 in FIG. 2.

Referring to FIG. 2 and FIG. 3, the artificial root 20 comprises an upper flange 100, a mid screw 110 and a lower portion 120.

A hexagonal projection 105 is formed on the upper flange 100 on which the connection column 30 is placed. A locking hole 65 and a stop-shoulder 125 are formed between an edge 115 of the lower end of the upper flange 100 and the mid screw 110 in order to prevent the artificial root 20 from boring excessively into the jawbone 45.

In order to facilitate the implanting of the artificial root 20 into the jawbone 45, a thread 130 is formed on the outer surface of the mid screw 110 for securing it into the insert hole 140. As shown in FIG. 4, cutting edges 135 are formed on the lower portion 120. The cutting edges 135 of the lower portion 120 partially cut the jawbone 45 with the screw of the artificial root 120; the mid screw 110 is implanted into the jawbone 45; the artificial root 20 is secured in the jawbone 45.

However, the above dental implants, currently in wide use, suffer from the disadvantage of using separate parts that are combined into a single artificial tooth.

Using the present art, it is necessary to implant the artificial root in one surgery, and then, after waiting about 3 to 6 months for the bone tissue to bond with the implanted fixture, the artificial crown must be secured to the fixture during a second surgery.

The disadvantages of this two-step process are obvious. The patient must suffer the physical, mental and financial burden of two surgeries; the patient must go three to six months without the replacement tooth; the patient must endure the pain and discomfort of two post-surgery periods of healing. Although some success has been reported with new designs that allow for connecting the abutment during the first surgery, the connection process remains cumbersome and time-consuming.

Also, there is a problem with the upper flange portion of the fixture where it comes in contact with the cortex bone. The fixture has a fine, machined surface in this area and is shaped into basically a cylindrical form. These characteristics contribute to osteolysis of the cortex bone because of the stress and shearing force that the bone is subjected to after the restoration when the patient is chewing.

The process of attaching a fixture to the jawbone using a single screw with a single thread is not easy. This technique also reduces the life of the implant because it leaves the jawbone subjected to heat. Also, it currently takes approximately 3 to 6 months for the bone to bond sufficiently with the implant to allow for the mounting of an artificial crown on the machined surface. These days, the necessary time for the bone-bonding process has been reduced with the development of various improved screw forms and surface treatments. Operations mounting an artificial crown immediately after the implanting of a fixture have succeeded in non-tooth jawbone, however, the restriction remains that the quality and quantity of remaining bone must be sufficient to facilitate this technique.

Also, implants connecting a fixture, an abutment and an artificial crown with a threaded connection suffer from slack in the structure as well as screw scraps created when the screw is tightened. This problem of slack remains unsolved, though the proper application of force when tightening the screw will minimize the problem and the development of a design that wedges the negative thread of the fixture against the positive thread of the abutment has also decreased this negative effect.

Also, in the area around the connection between fixture and abutment, bacteria can enter and multiply. This can cause inflammation around the gums. Also, the fibrous layers of the gums attach vertically and securely to the surface of a natural tooth while the fibrous layers of the gums are arranged horizontally or in a ring shape when they attach to an artificial fixture. In this latter case the bond is relatively weak and insecure.

Also, because the thread portion of the fixture uses a single thread with a pitch of about 0.6 mm on the surface of a lathe-treated cylinder, it is relatively likely to fail or "strip" in the soft bone because of a limited surface area and the resulting concentration of stress in this small area of bone. These days, double threads formed on a wedged cylinder decrease the problems encountered during operations, improve the stability of the implanted fixture, decrease the waiting time between operations, reduce the amount of heat generated by friction and spread the mechanical stress over a larger area of bone. However, the problem of limited surface area and stress distribution around the screw remain essential design flaws in the present art.

When using the related drill to bore a hole in the jawbone, generally, the shaved bone chips come out along the recesses of the cutting edge. This extraction of bone material is known to slow the bonding process. In the past, the surgical procedure took longer because all alveolus bone had to be removed and the hole had to be tapped before the fixture was implanted. However, due to recent advances, fixtures are now self-tapping, cutting down on the length of the procedure. The new problem created by this self-tapping process is that the loose trabecular bone impedes the bonding process.

Moreover, when coupling an artificial crown with a fixture immediately after the fixture is implanted, the artificial crown should be mounted on an abutment. The use of dental mucous resin, with blood shedding, makes the operation complicated and more time-consuming.

DISCLOSURE OF THE INVENTION

Considering the above-mentioned problems and disadvantages, it is one object of the present invention to provide a dental implant comprising a fixture and an abutment integrally formed with the fixture to accomplish simple implantation, good bone-to-fixture bonding and immediate mounting of an artificial crown thereon.

It is another object of the present invention to provide a dental implant having an improved structure in order to enhance initial reaction for curing of the bone and to efficiently spread the stress generated during chewing through the simple implantation of implant into the jawbone and the superior bonding between the fixture of the implant and the bone tissue.

It a still another object of the present invention to provide a dental implant including a settling portion having improved structure so as to prevent osteolysis of the cortex bone and maintain the original level of the alveolar bone after hard chewing.

It is a still another object of the present invention to provide a compaction drill having a specially designed head for implanting the implant into the jawbone.

To achieve the above-mentioned objects of the present invention, there is provided a dental implant comprising an upper abutment portion to which an artificial crown is fixed, a lower fixture portion for securing the implant in a jawbone, and a settling portion formed between the abutment portion and the fixture portion, wherein a bone tissue is bonded to the settling portion.

The implant further comprises a cutting and constriction means for cutting the bone tissue and for constricting bone chips, wherein the cutting and constriction means is formed at a lower portion of the fixture portion. The cutting and constriction means includes a first cutting edge, a second cutting edge and a third cutting edge which are upwardly formed from an end of the fixture portion for cutting the bone tissue. The cutting edges are respectively formed from the end of the fixture portion wherein inclined portions are upwardly formed from upper portions of the first, the second and the third cutting edges to constrict the bone chips. In this case, the first, the second and the third cutting edges have predetermined inclinations and are disposed on the lower fixture portion by the same interval.

A crown cap for fixing the artificial crown is mounted on the abutment portion. The crown cap has the inside shape corresponding to the shape of the abutment portion and is composed of acrylic resin.

The surface of said abutment portion is machined and surfaces of the settling and the fixture portions are treated by a blasting method to respectively have average surface textures of about 1.0 to about 2.0 $\mu$m. Also, the settling portion has a length of about 1 to about 3 mm corresponding to a cortex bone of the jawbone.

The abutment portion comprises an upper portion to which the artificial crown is fixed, a chamfer for forming edge portions of the implant, and a curved shoulder for maintaining closure of a junction epithelium and a connective tissue in the mouth. At that time, the curved shoulder further includes a tissue-affixed portion wherein a soft tissue is attached to the tissue-affixed portion. The upper portion of the abutment portion has a diameter upwardly reduced by an angle of about 4 to about 6° concerning a vertical axis and a portion of the upper portion of the abutment portion has an even surface and other portions of the upper portion of the abutment portion have circular surfaces.

An insertion groove for preventing the artificial crown from departing from the abutment is formed on the upper portion of the abutment portion A plurality of minute grooves are formed on the surface of the tissue-affixed portion and the tissue-affixed portion has a length of about 0.5 to about 1.5 min. In this case, each minute groove has a depth of about 15 to about 25 $\mu$m and is disposed by an interval of about 30 to about 50 $\mu$m. The diameter of the settling portion is gradually reduced from the upper abutment portion in a downward direction. A plurality of minute screwed grooves are formed on a surface of the settling portion and each minute groove has a pitch of about 0.15 to about 0.25 $\mu$m and a thread angle of about 80 to about 120°.

According to one preferred embodiment of the present invention, at least one thread is formed on a surface of the fixture portion and the thread has a depth of about 300 to about 500 $\mu$m and a pitch of about 700 to about 900 $\mu$m.

Also, according to another preferred embodiment of the present invention, a first thread and a second thread are alternately formed on a surface of the fixture portion. At that time, each of the first thread and the second thread has a depth of about 300 to about 500 $\mu$m and a pitch of about 700 to about 900 $\mu$m.

To accomplish the objects of the present invention, there is provided a head for a dental compaction drill comprising a guide corresponding to the front portion of the head for contacting with a jawbone, a first elimination edge prolonged from the guide in a first direction, a second elimination edge formed above the first elimination edge in a second direction, and a transposition portion formed between the first elimination edge and the second elimination edge. In this case, the first direction is opposed to the second direction.

The dental implant according to the present invention has the structure in which the abutment having the shape of the cylindrical projection is integrally formed with the fixture having the shape of the screw so as to mount the crown thereon after the fixture is implanted into the jawbone. The artificial crown can be attached to the cylindrical abutment immediately after the fixture is implanted and the chamfer of the abutment is shaped so as to easily form the edge portion of the crown.

The upper portion and the curved shoulder of the abutment are designed to limit plaque deposits and promote bonding with the soft bone-tissue. The blasting-treatments on the surfaces of the settling portion and the fixture produce average surface textures of about 1.4 $\mu$m in order to facilitate maximum bonding with the bone tissue.

The soft bone-tissue is attached to the curved shoulder having a predetermined curvature. The tissue-affixed portion of the curved shoulder to which a soft tissue is attached promotes a strong and tight bonding effect in conjunction with the adhesive layer and the mucous membrane of the mouth tightly bonded each other. The tissue-affixed portion of the curved shoulder is patterned with minute grooves having the depth of about 15 to about 25 $\mu$m and set at the interval of about 30~50 $\mu$m. The minute grooves promote bonding with the bone tissue.

The settling portion attached to the cortex bone of the jawbone. The settling portion having the length of about 2 mm includes micro screwed grooves having the pitch of about 0.2 mm and the thread-angle of about 80 to about 120°. The settling portion restrains the fixture portion from sinking.

The trapezoidal thread formed on the fixture portion increases the surface area of the fixture portion and forms an advantageous structure for stress dispersion. Double threads, having the depth of about 400 $\mu$m and the pitch of about 500 $\mu$m, are formed on the portion implanted into the soft bone-tissue, while a single thread, having the depth of about 400 $\mu$m and the pitch of about 800 $\mu$m, is formed on the portion implanted into solid bone-tissue. The bottom end of the thread, about 3 mm in length, forms the conical portion reduced to bottom tip, thereby easily implanting the fixture portion into the jawbone. The cut bone-chips from three cutting edges at the bottom of the fixture are constricted by inclinations. When the soft bone-tissue is partially eliminated by the head for the compaction drill, the first elimination edge of the head is formed opposite to the second elimination edge of the head, whereby promoting the bone constriction.

According to the present invention, the fixture portion achieves greater strength than the conventional fixture and improves the stability of the soft bone-tissue attached to the implant of the present invention.

Also, with regard to the improved structure of the abutment portion and the fixture portion, the implant of the present invention has increased initial fixing stability and enlarged surface area so that bonding reaction between the jawbone and the implant is accelerated. In addition, the crown can be attached immediately after the fixture portion is implanted, thereby promoting the effective closure.

Furthermore, the invention provides the dental compaction drill that comprises the special head used for implanting the dental implant of the present invention and can remarkably improve bonding bone tissue with the implant.

BRIEF DESCRIPTION OF THE DRAWINGS

The above objects and other advantages of the present invention will become more apparent by describing in detail the preferred embodiments thereof with reference to the attached drawings in which.

BEST MODES FOR CARRYING OUT THE INVENTION

Hereinafter, various embodiments of the present invention will be explained in more detail with reference to the accompanying figures, however, it is understood that the present invention should not be limited to the following preferred embodiments set forth herein.

Figure 1:
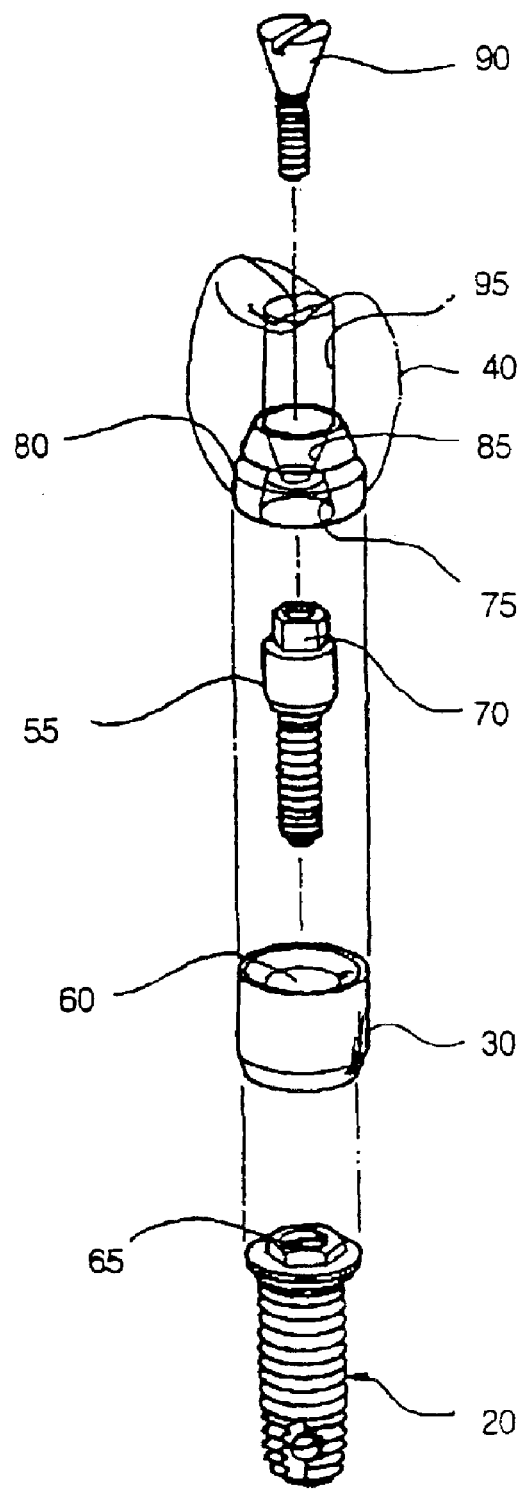
FIG. 1 is an exploded perspective view for showing the conventional implant for the artificial crown.
Figure 2:
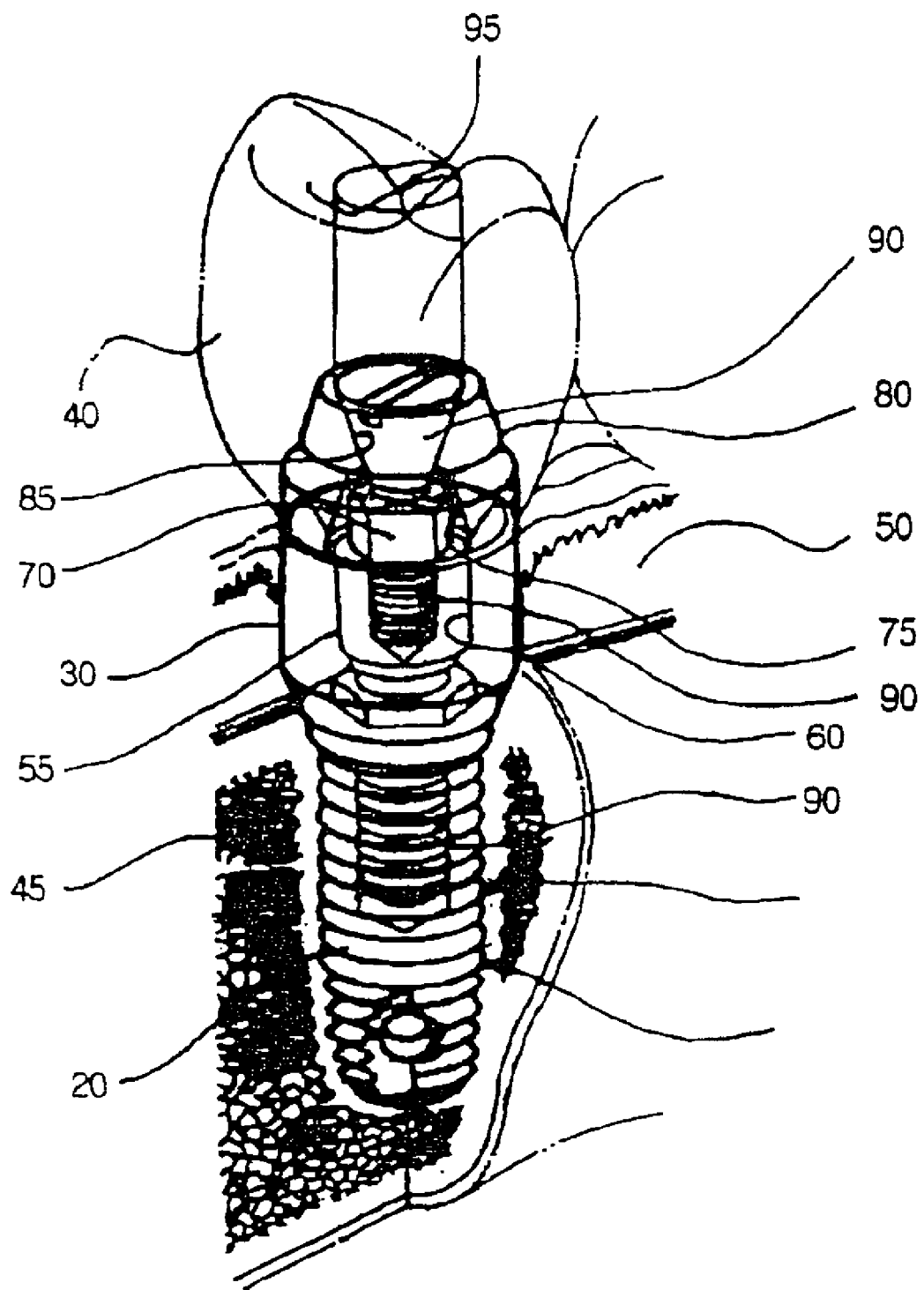
FIG. 2 is a transparent perspective view for explaining the implant in FIG. 1 where the artificial crown is mounted.
Figure 3:
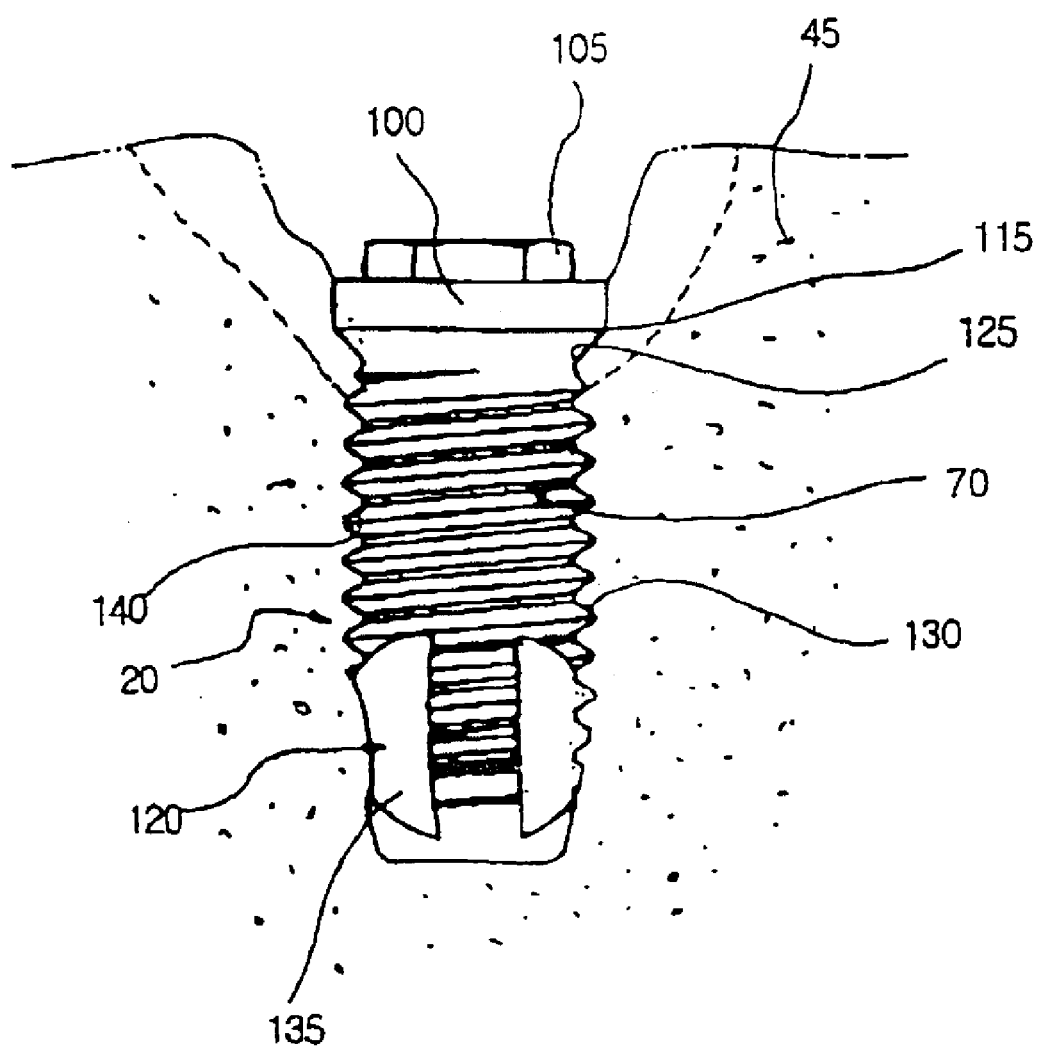
FIG. 3 is an enlarged cross-sectional view for showing the artificial implant implanted into the jawbone in FIG. 2.
Figure 4:
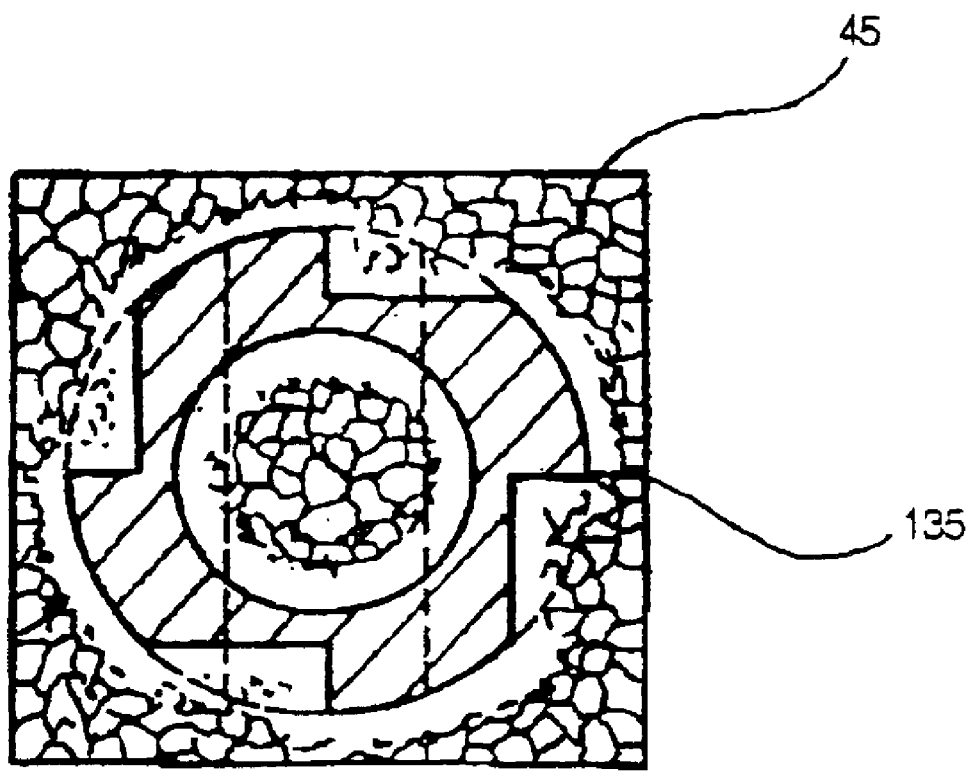
FIG. 4 is an enlarged bottom view for showing the bottom of the artificial implant implanted into the jawbone in FIG. 2.
Figure 5:
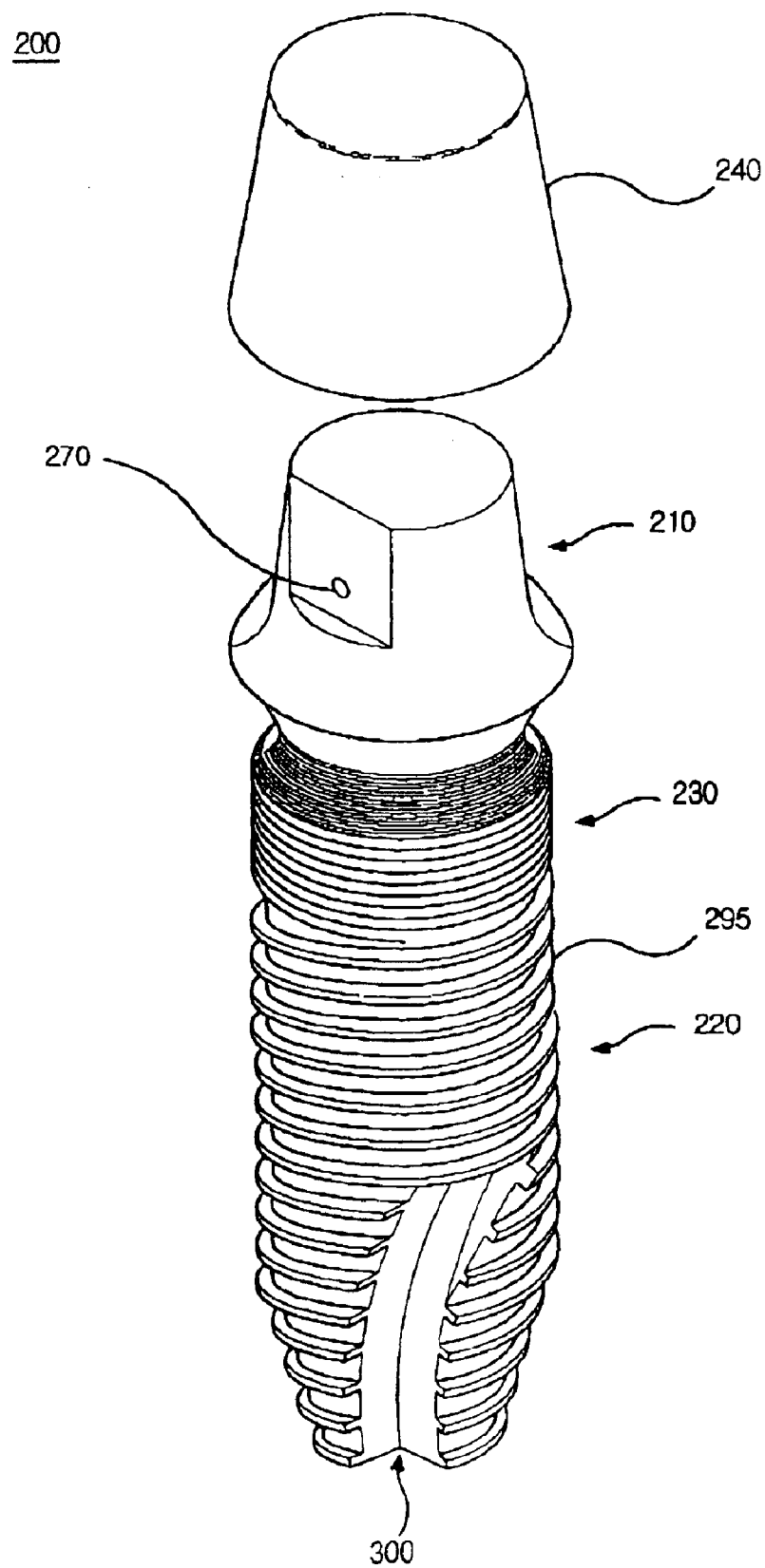
FIG. 5 is a perspective view for showing a dental implant according to one preferred embodiment of the present invention.
Figure 6:
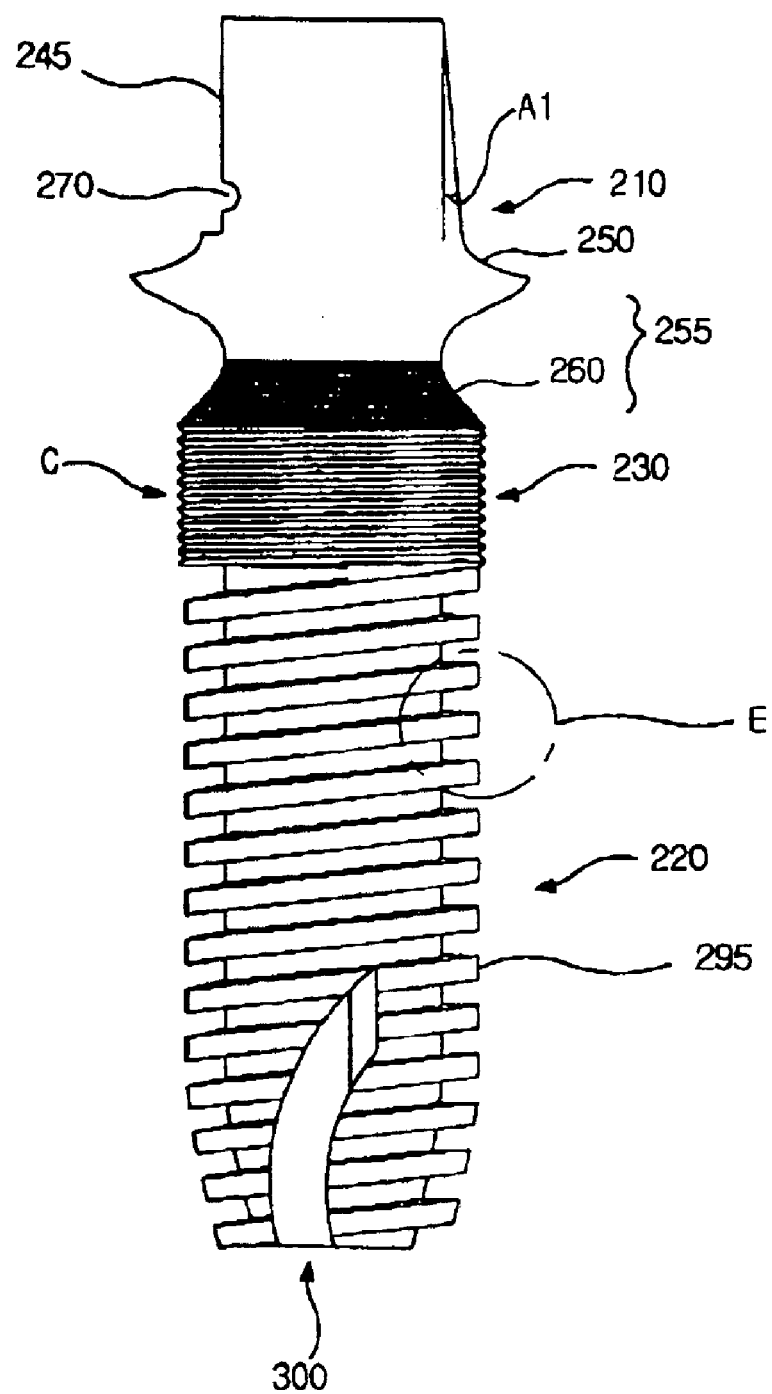
FIG. 6 is an enlarged side view for illustrating the dental implant in FIG. 5.

FIG. 5 is a perspective view for showing a dental implant according to one embodiment of the present invention and FIG. 6 is an enlarged side view for illustrating the dental implant in FIG. 5.

Referring to FIGS. 5 and 6, a dental implant 200 according to the present embodiment includes an upper abutment portion 210, a lower fixture portion 220 and a settling portion 230 formed between the abutment portion 210 and the fixture portion 220. Those portions 210, 220 and 230 are integrally formed. A crown cap 240 is mounted on the abutment portion 210 and adapted as the artificial crown.

The surface of the abutment portion 210 is generally machined. The surfaces of the fixture and the settling portions 220 and 230 are preferably treated to have average surface textures of about 1.4 μm by blasting method with silica or bio-glass having the diameter of about 75 μm. In other words, when the attached area of the fixture portion 220 implanted into the jawbone has the average surface texture of about 1.4 μm, the contact area of the jawbone attached such area the fixture portion 220 can be increased.

In general, the implant 200 has the length of about 18.0 mm and the diameter of about 4.0 mm when the implant 200 is implanted into the jawbone. In this case, the abutment portion 210 has the length of about 6 mm, the settling portion 230 has the length of about 2 mm and the fixture portion 220 has the length of about 10 mm, respectively. Also, the diameter of the abutment portion 210 is about 5 mm, the diameter of the upper portion of the settling portion 230 is about 4.2 mm, and the diameter of the fixture portion 220 is about 4.0 mm, respectively. However, the dimension of the implant 200 and the ratios of the lengths and diameters of those portions 210, 220 and 230 can be various depending on the conditions to which the implant 200 is subjected.

According to the present invention, the length of the settling portion 230 hardly varies no more than about 2 mm but the length of the fixture portion 220 can be various within the range of about 4 to about 15 mm according to the locations and conditions of the implant 200. Also, the length of the lower tissue-affixed portion of the abutment portion 210 hardly varies no more than about 1 mm since the thickness of the soft tissue in the mouth is usually regular, but the length of the upper abutment portion 210 can vary according to locations and conditions of the implant 200.

As it is described above, when the abutment portion 210, the settling portion 230 and the fixture portion 220 are integrally formed according to the present invention, the implant of the present invention has remarkably increased compared with the conventional implant whose the elements are separated. In addition, the implant of the present invention maintains the soft-tissue-affixed portion differently from the conventional implant. The invention can close leukocyte infiltrated connective tissue (LCT) at the source and can improve the stabilization of the soft-tissue-affixed portion.

Figure 7:
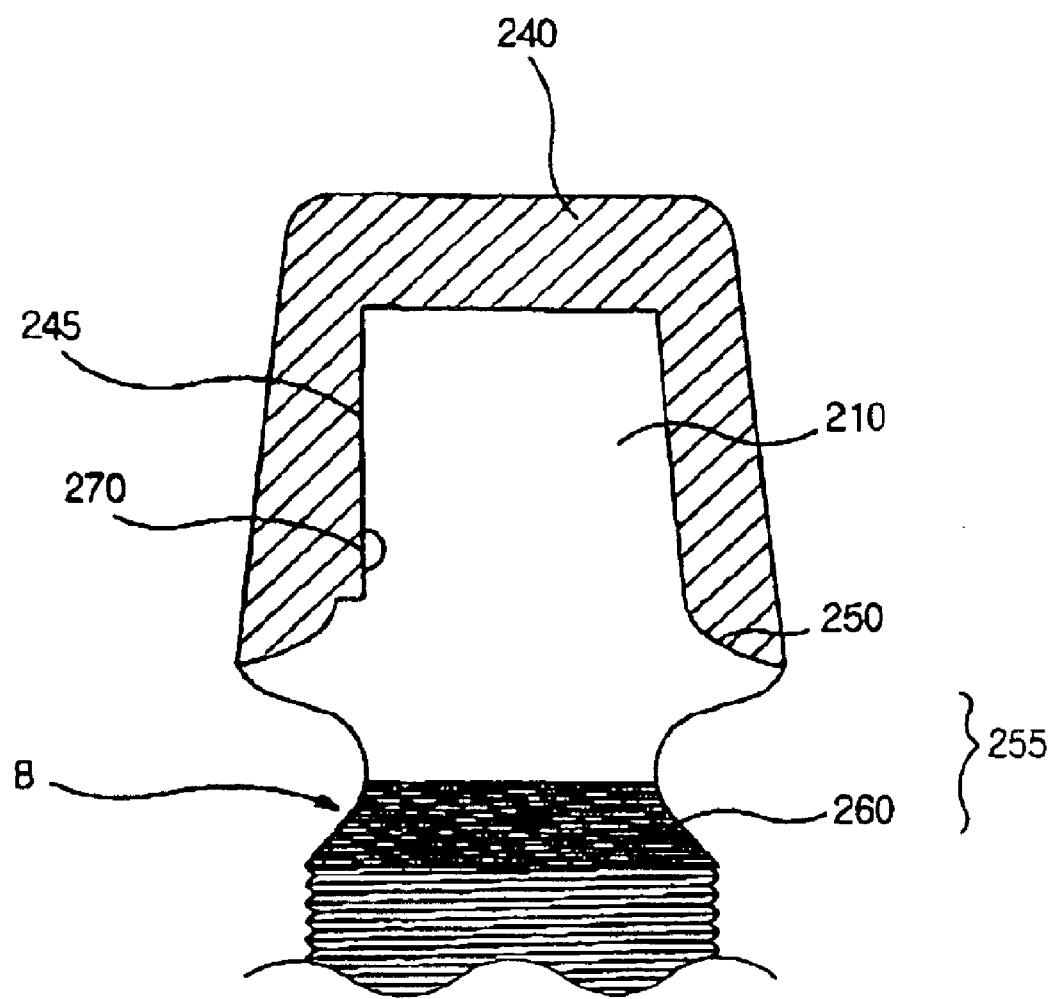
FIG. 7 is an enlarged side view for illustrating an upper portion of the implant including an abutment portion in FIG. 6.

FIG. 7 is an enlarged side view for showing the upper portion of the implant 200 including the abutment portion 210 on which the crown cap is mounted in FIG. 6.

Referring to FIGS. 6 and 7, the abutment portion 210 comprises an upper portion 245 covered with the crown cap 240, a chamfer 250 and a curved shoulder 255. A tissue-affixed portion is formed at the lower portion of the curved shoulder 255.

The upper portion 245 of the abutment portion 210 has the diameter upwardly reduced from the chamfer 250. Preferably, as shown in $A_1$ of FIG. 6, the upper portion 245 of the abutment portion 210 has the diameter upwardly reduced by the angle of about 4–6°, preferably about 5° concerning the vertical axis.

One portion of the upper portion 245 of the abutment portion 210 is machined to have the flat shape and other portions of the upper portion 245 have the cylindrical shape. Because the upper portion 245 of the abutment portion 210 is formed like a round with one side cut flat, the upper portion 245 can rotate connected with a mount (not shown) used for the implanting of the implant 200. Also, a insertion groove 270 is formed on the flat-side surface of the upper portion 245 so that when the implant 200 is rotated into the jawbone for implanting, the projection formed on the mount for rotating the implant 200 is inserted in the insertion groove 270, thereby increasing the coupling force of the implant 200 and the mount. Hence, when the implant 200 is rotated with the mount, the coupling of the insertion groove 270 and the projection can prevent the mount from separating from the implant 200.

The above-described upper portion 245 of the abutment portion 210 is covered with the crown cap 240 to complete the restoration. The crown cap 240 has the inside shape corresponding to the shape of the upper portion 245 of the abutment portion 210. The crown cap 240 is composed of acrylic resin. The artificial crown can be coupled with the implant immediately by using the crown cap 240, serving as a temporary crown.

The chamfer 250 of the abutment portion 210 is designed to minimize the partial elimination of the abutment portion 210 so as to form edge portions near the gums when the implant 200 is in place.

The curved shoulder 255 of the implant 200 is abruptly curved toward the inside and prolonged from the chamfer 250. The curved shoulder 255 contacts the soft tissue after the implant 200 is in place. The curved shoulder 255 is so-called "Monroe's Waist". The caved shoulder 255 is formed to have the abrupt inclination, thereby creating the effective closure between the junction epithelium and the connective tissue. Therefore, the curved shoulder 255 enhances the soft-tissue stabilization of the implant 200 and prolongs the life of the implant 200.

Figure 8:
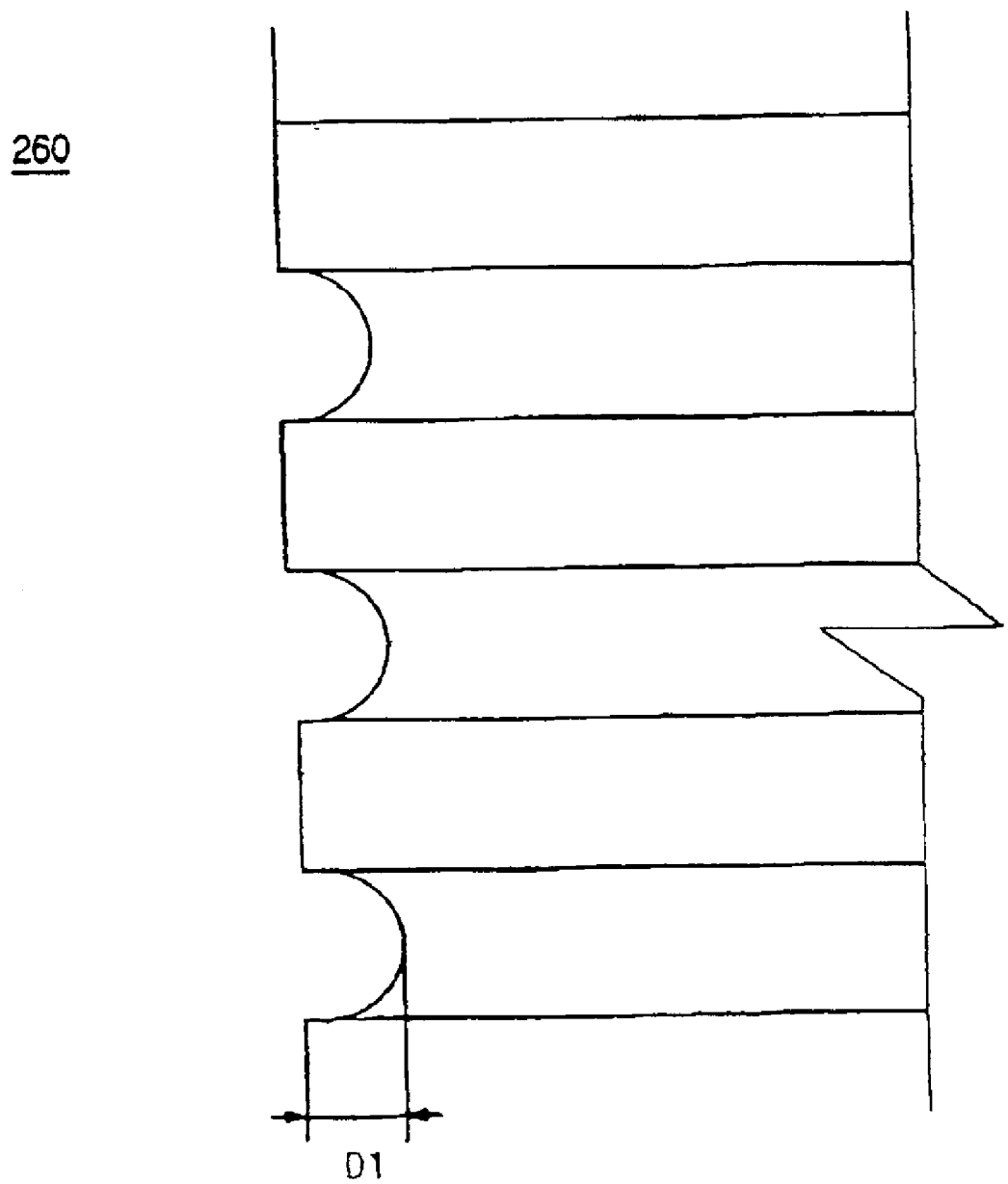
FIG. 8 is an enlarged side view of 'B' in FIG. 7.

FIG. 8 is an enlarged side view for showing 'B' in FIG. 7.

Referring to FIGS. 6 to 8, the tissue-affixed portion 260 of the abutment portion 210 has the diameter-increasing structure from the curved shoulder 255 to the abutment portion 210. As shown as $A_2$ and $D_1$ in FIG. 8, the tissue-affixed portion 260 is patterned with a number of minute grooves having the depth of about 15~25 μm and the intervals of about 30~50 μm. Hence, when the implant 200 is in place, the effective connection-tissue zone can be formed between the soft tissue and the implant 200 through accelerating the growth of the soft-tissue fibrocyte and controlling the direction of fiber growth. Thus, the tissue-affixed portion 260 can be referred to the biologic grip zone. According to the present invention, the tissue-affixed portion 260 of the curved shoulder 255 has the length of about 1 mm.

Figure 9:
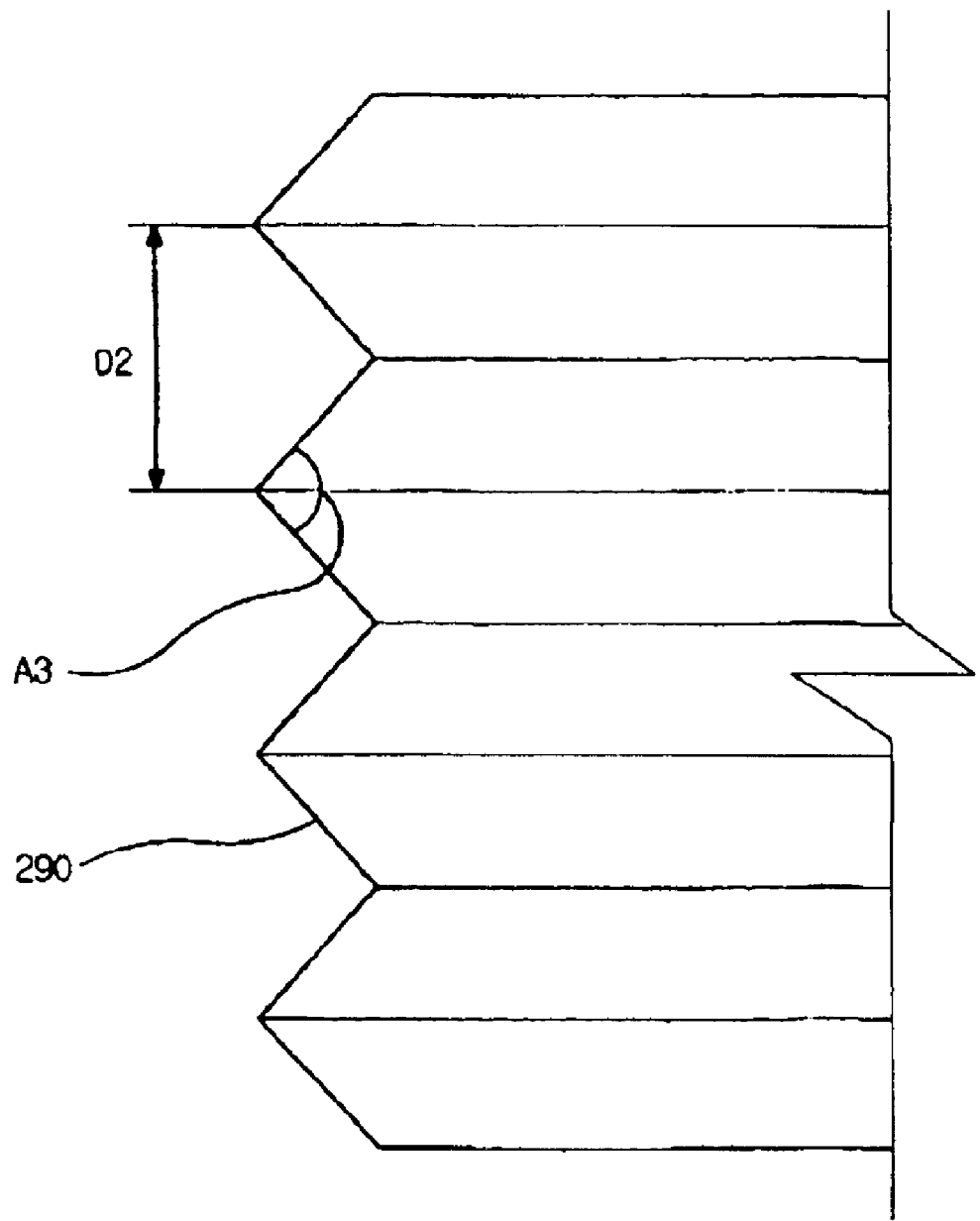
FIG. 9 is an enlarged side view of 'C' in FIG. 6.

FIG. 9 is an enlarged side view for illustrating 'C' in FIG. 6.

Referring to FIGS. 6 and 9, the settling portion 230 has the diameter gradually reduced from the curved shoulder 255 in the downward direction. That is, the upper portion of the settling portion 230 implanted in the jawbone has the diameter of about 4.2 mm, however, the diameter of the lower portion of the settling portion 230 is about 4.0 mm, so the diameter of the upper portion is greater than that of the lower portion.

As shown in FIG. 9, a number of minute screwed grooves 290 are formed on the surface of the settling portion 230. The screwed grooves 290 have the pitch ($D_2$) of about 0.15 to about 0.25 mm, preferably about 0.20 mm and the thread angle ($A_3$) of about 80 to about 120°. The settling portion 230, like a wise crystal module, can disperse the stress on the implant 200 into the cortex-bone of the jawbone and minimize osteolysis so as to increase the bond with the bone. That is, the conventional implants causes ostcolysis of the cortex-bone due to the cylindrical contact surface where the implant meets the cortex bone, however, the implant of the present invention has numerous minute screwed grooves 290 on the surface of the settling portion 230 attached to the cortex bone, and as a result, the minute screwed grooves 290 improve the bond with the cortex bone and disperse the stress transferred through the implant 200.

Figure 10:
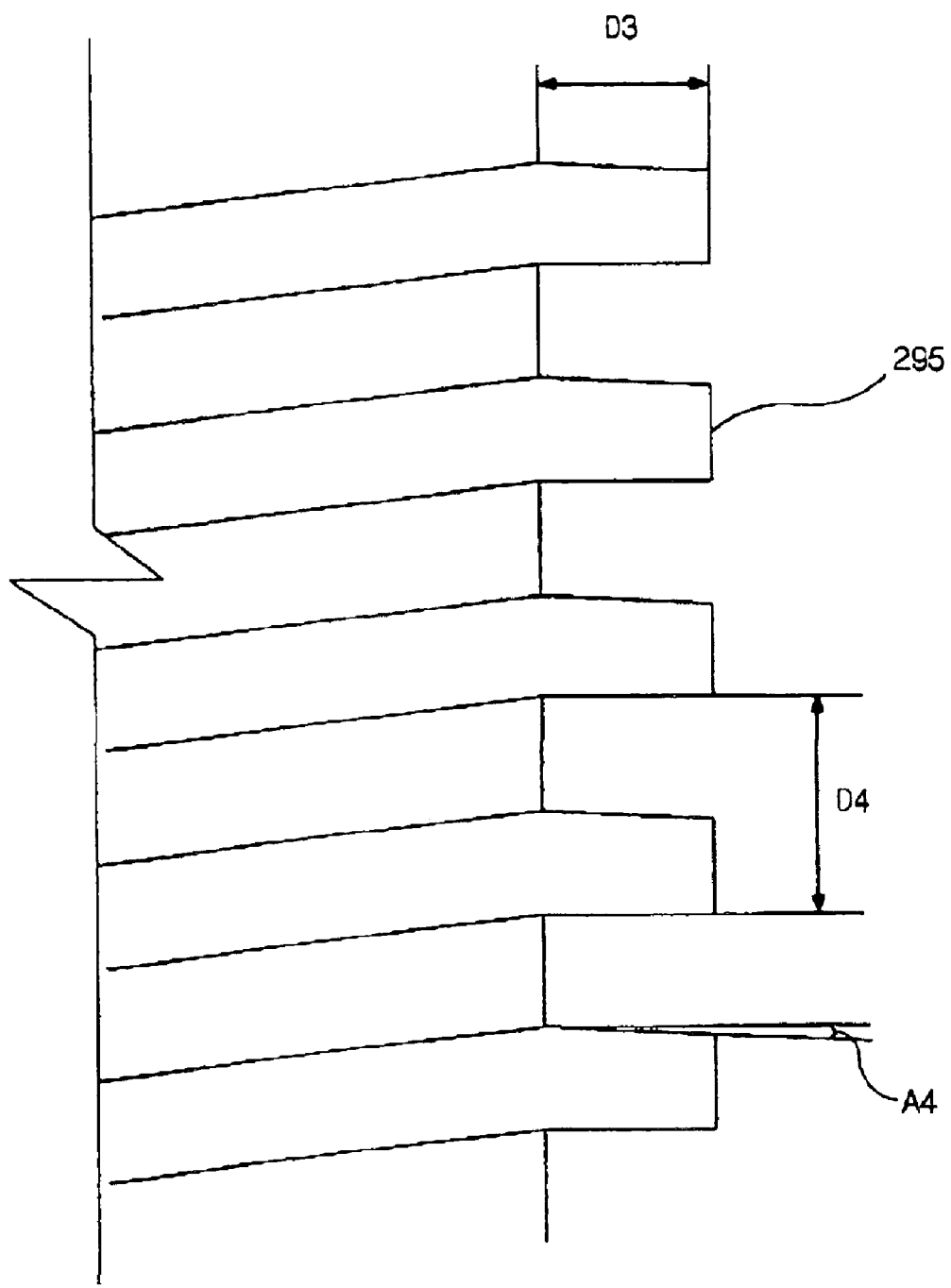
FIG. 10 is an enlarged side view of 'E' in FIG. 6.

FIG. 10 is an enlarged side view of 'E' in FIG. 6.

Referring to FIGS. 6 and 10, the fixture portion 220 is connected to the settling portion 230 and implanted into the jawbone. The upper portion of the fixture portion 220 has the diameter of about 4.0 mm and the lower end diameter of the fixture portion is about 2.0 mm. The fixture portion 220 has the sharply reduced diameter about the lower end of the cylindrical body. Threads 295 are formed on the surface of the fixture portion 220 to implant the implant 200 into the jawbone according as the threads 295 on the fixture portion 220 rotate.

In the present embodiment, the threads 295 have the shape of the trapezoidal power thread as shown in FIG. 10 and is formed on the surface of the fixture portion 220. The threads 295 have the pitch of about 800 μm, the top-face angle of about 3° and the bottom-face angle of about 0°. Thus, the contact area of the fixture portion 220 about the jawbone can be increased the stress applied to the implant 200 can be easily dispersed by the threads 295.

Figure 11:
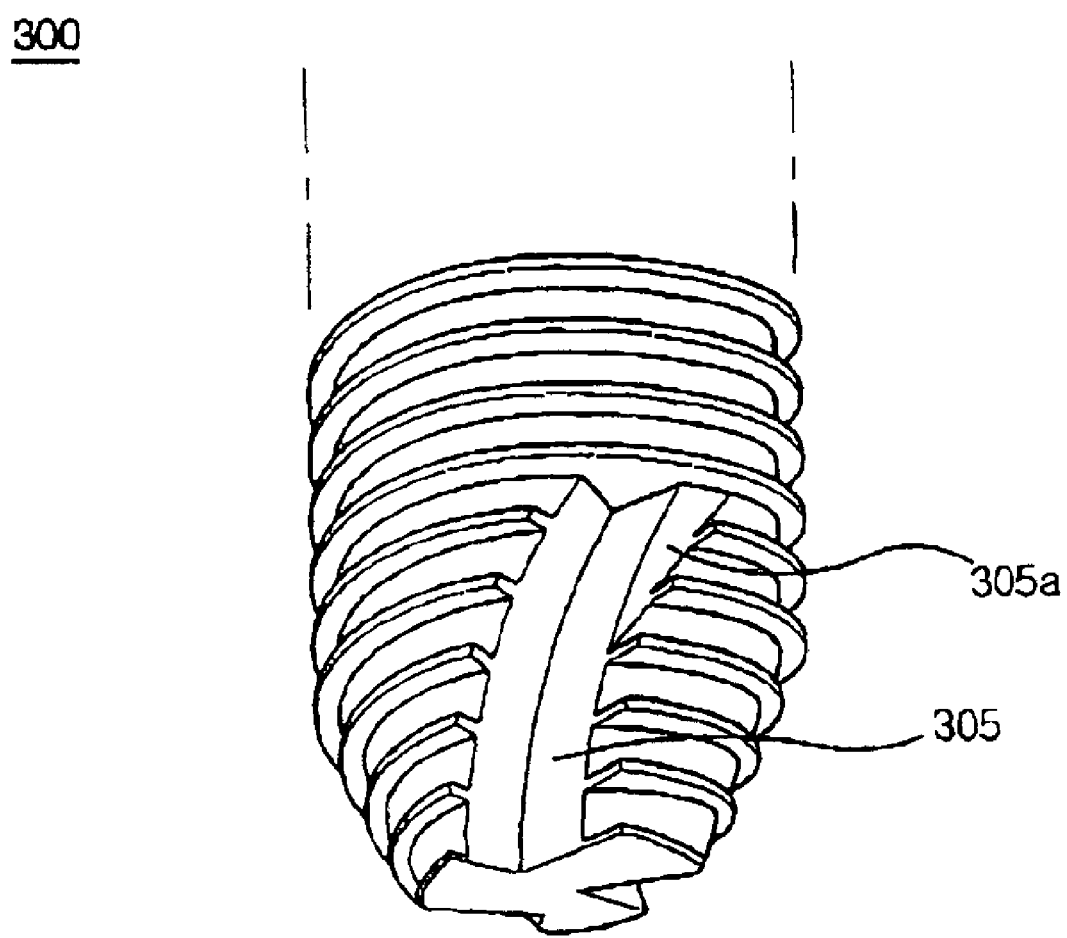
FIG. 11 is an enlarged perspective view of 'F' in FIG. 5.
Figure 12:
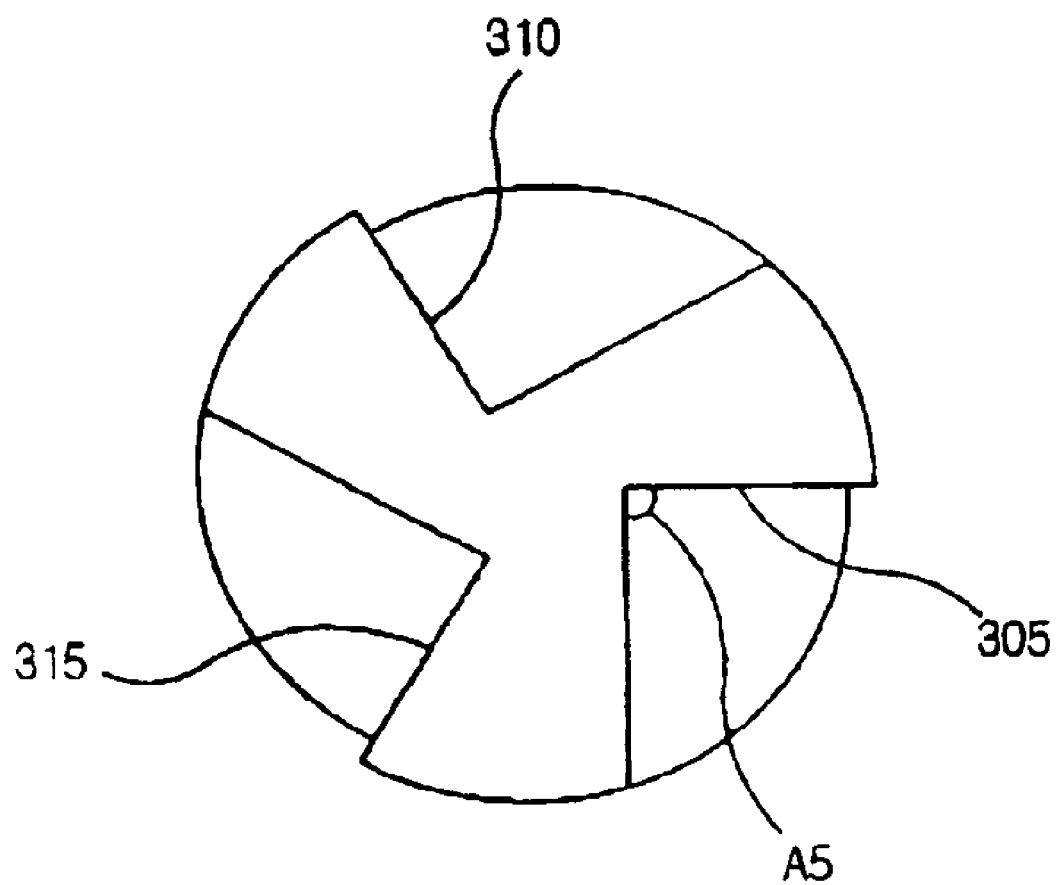
FIG. 12 is a bottom view of the implant in FIG. 11.

FIG. 11 is an enlarged perspective view of 'F' in FIG. 5 and FIG. 12 is a bottom view of the implant in FIG. 11.

Referring to FIGS. 5, 11 and 12, a cutting and constriction means 300 for cutting the bone tissue and constricting bone chips is formed on the lower tip of the fixture portion 220. The cutting and constriction means 300 helps with the easy placing of the implant 200 and promotes the stability of the implant 200. The cutting and constriction means 300 includes a first cutting edge 305, a second cutting edge 310 and a third cutting edge 315, which are upwardly formed from an end of the fixture portion 220 and are partially cut at the angle of about 90°. The cutting and constriction means 300 also includes inclined portions 305a with inclined surfaces upwardly formed from the an upper portion of the cutting edges 305, 310 and 315 by the predetermined angle. The first, the second and the third cutting edges 305, 310 and 315 are placed at equal angles.

During the implant 200 is implanted into the jawbone, the bone chips are separated from the jawbone come out through the cutting edges 305, 310 and 315 and the inclined portions 305a and the bone chips are accumulated in the inclined portions 305a of the upper portion of the cutting edges 305, 310 and 315. According to the present embodiment the bone chips separated from the jawbone are constricted around the fixture portion 220 and pressed by the cutting and constriction means 300, thereby increasing the bone density around the fixture portion 220. As a result, the stability of the implant 200 is improved and the time demanded to bond the bone tissue with the implant 200 is remarkably reduced.

Figure 13:
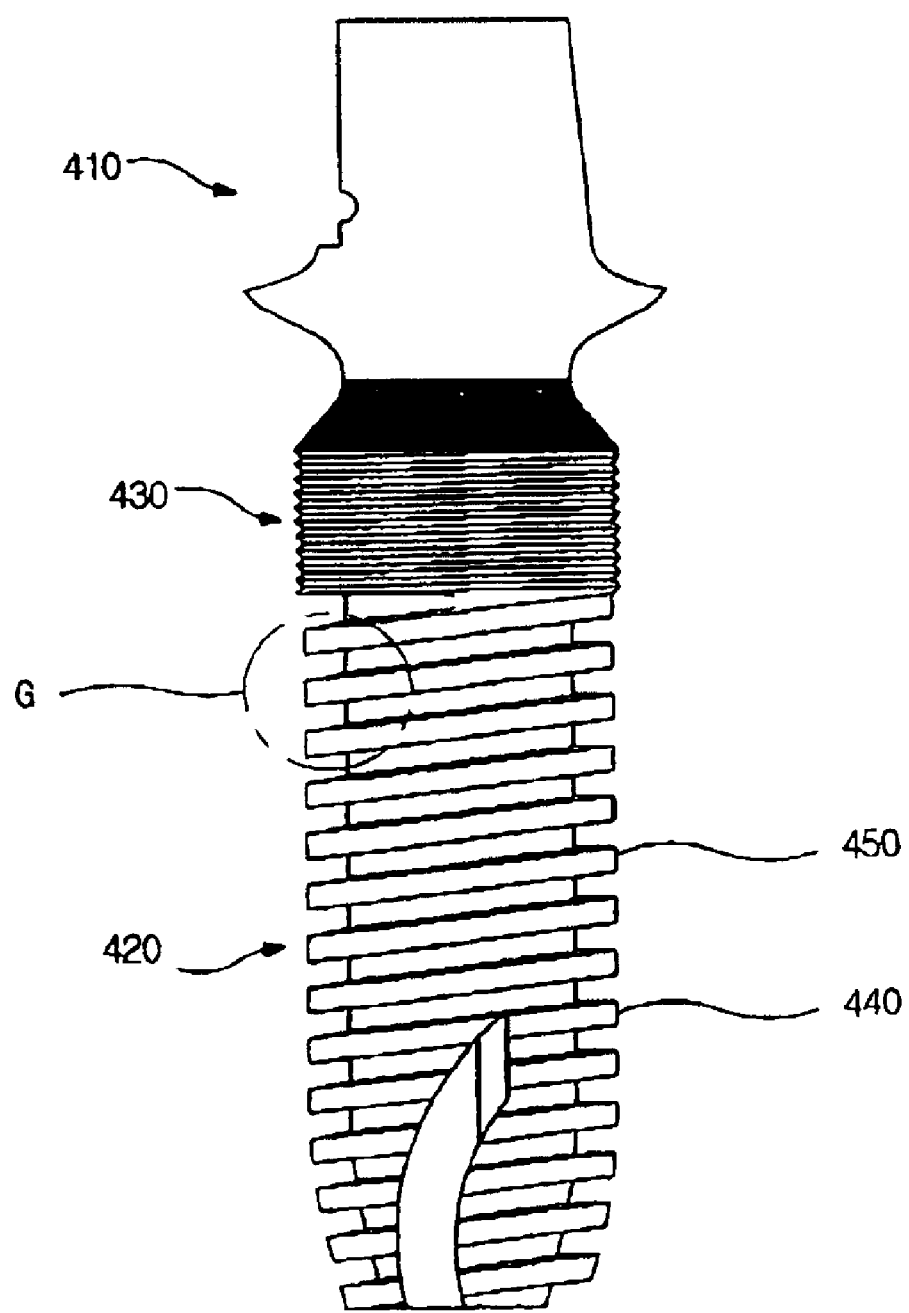
FIG. 13 is a side view for showing a dental implant according to another embodiment of the present invention.

FIG. 13 is a side view of a dental implant according to another embodiment of the present invention.

Referring to FIG. 13, a dental implant 400 of the present embodiment comprises an upper abutment portion 410, a lower fixture portion 420 and a settling portion 430 between the abutment portion 410 and the fixture portion 420.

In the present embodiment, except for the double threads formed on the surface of the fixture portion 420 with different pitch intervals, the abutment portion 410 and the settling portion 430 are identical to those of the above-described embodiment, so a description thereof is not included here.

Figure 14:
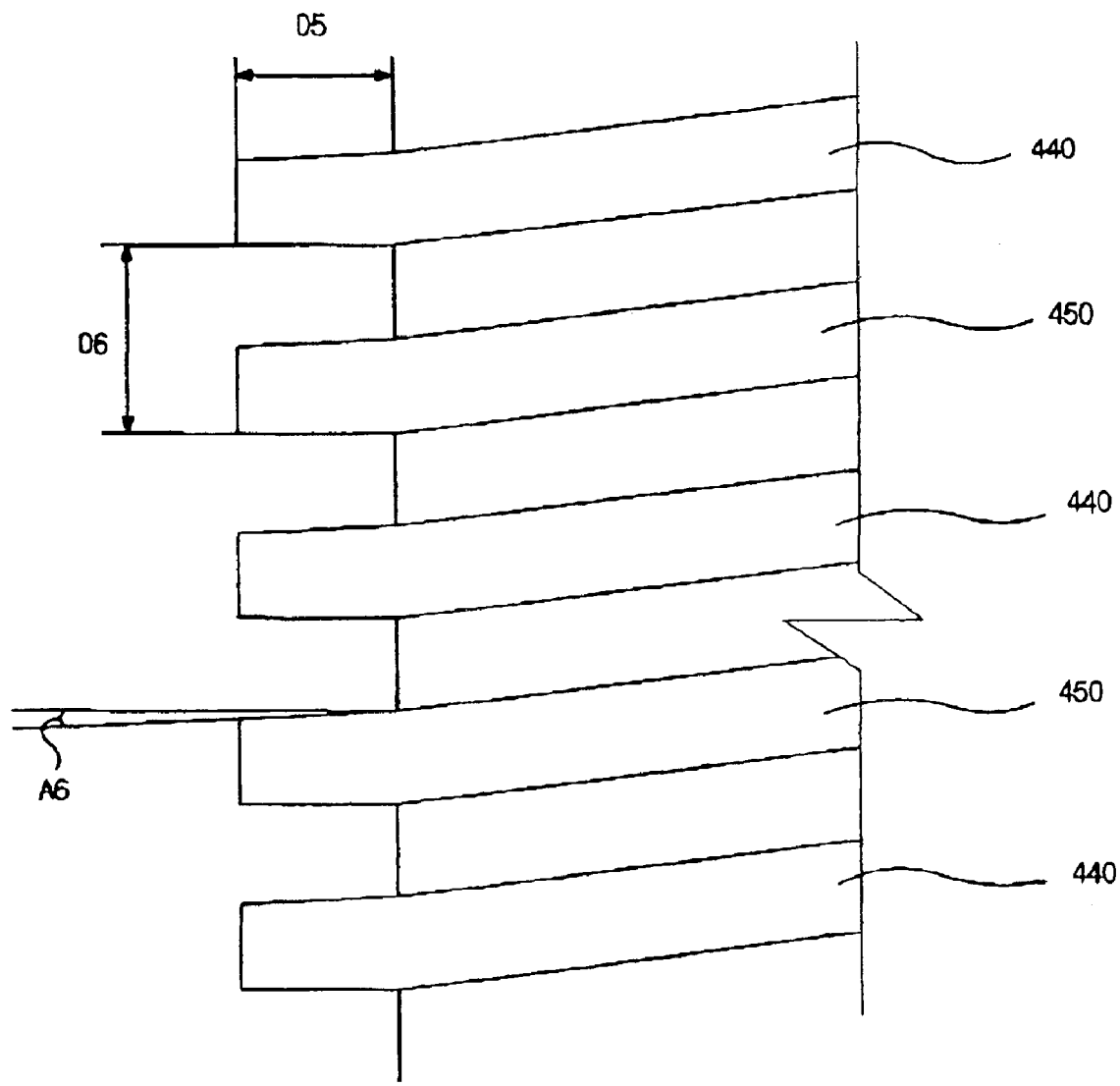
FIG. 14 is an enlarged cross-sectional view of 'G' in FIG. 13.

FIG. 14 is an enlarged sectional view of 'G' in FIG. 13.

Referring to FIGS. 13 and 14, a first thread 440 and a second thread 450 are formed on the surface of the fixture portion 420. The first and the second threads 440 and 450 respectively have the depth of about 400 μm $D_5$ and the pitch of about 500 μm $D_6$. The first and the second threads 440 and 450 also respectively have the top surface angle of about 3° $A_6$ and the bottom surface angle of about 0°. According to the present embodiment, the double threads including the first and the second threads 440 and 450 formed on the surface of the fixture portion 420 can shorten the length of time needed for implanting the implant 400 and reduce friction and heat-generation during the process for implanting the implant 400. Thus, the double threads more easily implants the fixture portion 420 into the jawbone as well as increases the strength of the bond between the bone tissue and the fixture portion 420.

Figure 15:
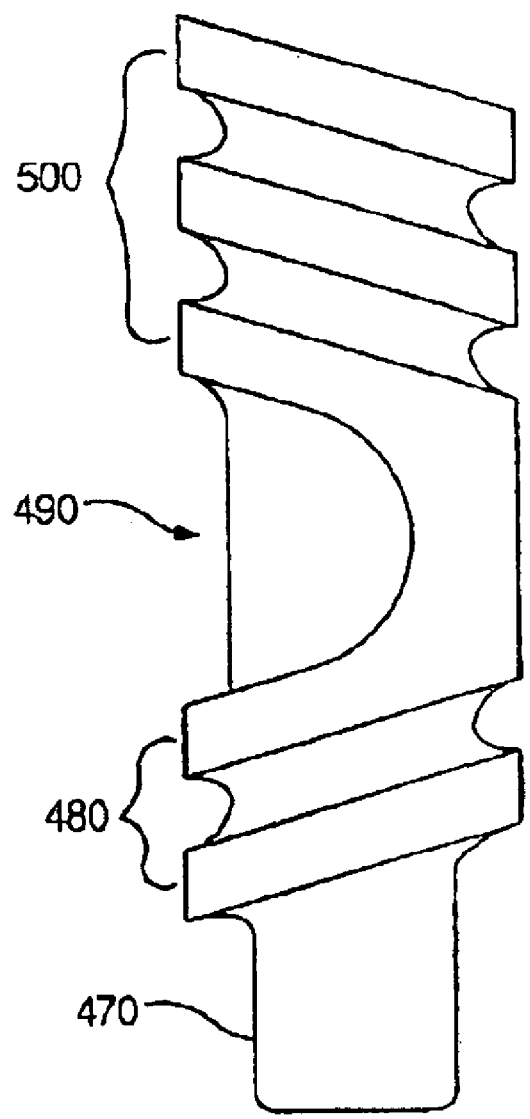
FIG. 15 is a plan view for showing a head of a dental compaction drill according to still another embodiment of the present invention.
Figure 16:
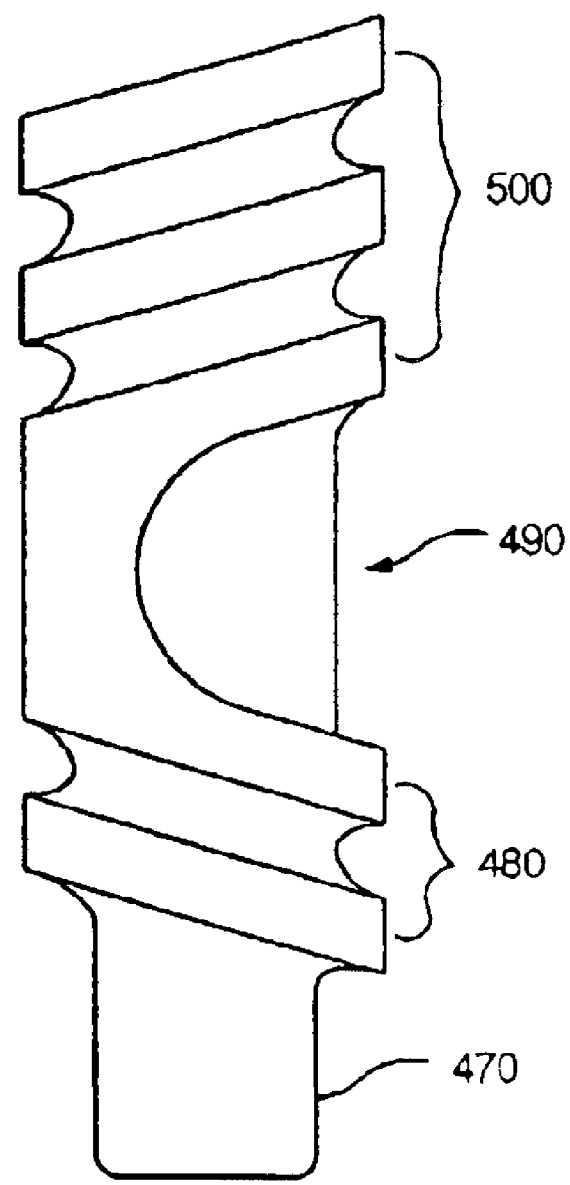
FIG. 16 is a bottom view of the head of the dental compaction drill in FIG. 15.

FIG. 15 is a plan view for showing a head for a dental compaction drill according to the present invention and FIG. 16 is a bottom view of the head for the dental compaction drill in FIG. 15.

Referring to FIGS. 15 and 16, the head 460 for the compaction drill according to the present invention comprises a guide 470 at one end thereof, a first elimination edge 480 prolonged from the guide 470, a second elimination edge 500 above the first elimination edge and a transposition portion 490 between the first and the second elimination edges 480 and 500. The compaction drill is used to form a hole with the ideal diameter in which to place the implant.

The head 460 for the compaction drill includes the first elimination edge 480 tuning in a first direction on a lower portion of the head 460 and the second elimination edge 500 turning in a second direction opposed to the first direction, thereby forming the trapezoidal transposition portion 490 of the first and the second elimination edges 480 and 500. The transposition portion 490 is formed about 3 mm apart from the bottom of the head 460. The maximum diameter of the head 460 is about 3.3 mm and the diameter of the guide 470 is about 2 mm. After a smaller-size drill makes a hole of a diameter of about 2 mm in the jawbone, the guide 470 can easily progress into the hole.

When the head 460 of the compaction drill makes the hole before placing the implant in the jawbone, some bone chips separated from the jawbone by the first elimination edge 480 are pushed up to the trapezoidal transposition portion 490 and other bone chips separated from the bone by the second elimination edge 500 are pushed down to the transposition portion 490. So, the bone chips separated from the jawbone by both of the elimination edges 480 and 500 are finally compressed around the transposition portion 490. Thus, the head 460 of the present invention increases the density of the bone while forming the hole in the bone. Particularly, when forming a hole in soft bone, the drill prevents bone chips from escaping and the implant placed in the hole formed by the head 460 bonds with the separated bone tissue earlier than the implant by the head 460.

Although the preferred embodiments of the present invention have been described, it is understood that the present invention should not be limited to those preferred embodiments, but various changes and modifications can be made by one skilled in the art within the spirit and scope of the invention as hereinafter claimed.

Industrial Applicability

According to the present invention, the dental implant is provided in which the upper abutment portion having the shape of the cylindrical projection interposes in the soft tissue and forms single-thread or double-thread fixture portions. This provides for the more complete bonding between hone tissue and implant which in turn makes for the more stable restoration.

Also, the structural improvement of the abutment and fixture portions further facilitates bonding between the implant and the jawbone by shortening the healing time and by increasing the contact area of surfaces between the jawbone and the implant. According to the present invention, the artificial crown can be mounted on the implant immediately after the implant is in place, thereby effectively sealing the area where the implant is positioned. The fixture portion of the present invention has specially designed shapes of drills and cutting edges and single/double threads. Hence, the placement of the implant is easy, early healing is promoted, the second surgery is unnecessary, all portions are incorporated into one body and fewer connections mean fewer places where the unit can become loosened and unstable.

Also, the reductions of pitches of the grooves and the threads facilitate early bone recovery, increase the quality of the bone adhesion and disperse the chewing stress uniformly. The increase in thread depth and the blasted surface do, too. The invention facilitates the mounting of crowns immediately after the implanting of the fixture.

Furthermore, micro threads formed on the blast-treated surface that contacts the cortex bone can disperse stress well, promote bone recovery and minimize osteolysis of the cortex bone.

What is claimed is:

1. A dental implant comprising:
   an upper abutment portion to which an artificial crown in fixed;
   a lower fixture portion for securing said implant in a jawbone; and
   a settling portion formed between said abutment portion and said fixture portion,
   wherein a bone tissue is bonded to said settling portion and a diameter of said settling portion is gradually reduced from said upper abutment portion in a downward direction,
   wherein said upper abutment portion, said lower fixture portion and said settling portion are formed unitarily and in one piece,
   wherein a crown cap for fixing said artificial crown is mounted on said abutment portion,
   wherein a surface of said abutment portion is machined and surfaces of said settling and said fixture portions are treated by a blasting method,
   wherein said abutment portion further comprises:
   an upper portion to which said artificial crown is fixed;
   a chamfer for forming edge portions of said implant; and
   a curved shoulder for maintaining closure of a junction epithelium and a connective tissue in the mouth,
   wherein a plurality of minute screwed grooves are formed on a surface of said settling portion.

2. The dental implant according to claim 1, further comprising a cutting and constriction portion configured to cut the bone tissue and to constrict bone chips, wherein said cutting and constriction portion is formed at a lower portion of said fixture portion.

3. The dental implant according to claim 2, wherein said cutting and constriction portion comprises a first cutting edge, a second cutting edge and a third cutting edge which are upwardly formed from an end of said fixture portion for cutting the bone tissue, said cutting edges being respectively formed from the end of said fixture portion wherein inclined portions are upwardly formed from upper portions of said first, said second and said third cutting edges to constrict the bone chips.

4. The dental implant according to claim 3, wherein said first, said second and said third cutting edges have predetermined inclinations and are disposed on said lower fixture portion by the same interval.

5. The dental implant according to claim 1, wherein said crown cap has an inside shape corresponding to a shape of said abutment portion and is composed of an acrylic resin.

6. The dental implant according to claim 1, wherein average surface textures of said settling and said fixture portions are between about 1.0 $\mu$m and about 2.0 $\mu$m.

7. The dental implant according to claim 1, wherein said settling portion has a length of about 1 to about 3 mm corresponding to a cortex bone of the jawbone.

8. The dental implant according to claim 1, said curved shoulder further comprising a tissue-affixed portion wherein a soft tissue is attached to said tissue-affixed portion.

9. The dental implant according to claim 8, wherein a plurality of minute grooves are formed on a surface of said tissue-affixed portion and said tissue-affixed portion has length of about 0.5 to about 1.5 mm.

10. The dental implant according to claim 9, wherein each minute groove has a depth of about 15 to about 25 $\mu$m and is disposed by an interval of about 30 to about 50 $\mu$m.

11. The dental implant according to claim 1, wherein said upper portion of said abutment portion has a diameter upwardly reduced by an angle of about 4 to about 6° concerning a vertical axis and a portion of said upper portion of said abutment portion has an even surface and other portions of said upper portion of said abutment portion have circular surfaces.

12. The dental implant according to claim 1, wherein an insertion groove for preventing said artificial crown from departing from said abutment is formed on said upper portion of said abutment portion.

13. The dental implant according to claim 1, wherein each minute groove has pitch of about 0.15 to about 0.25 mm and a thread angle of about 80 to about 120°.

14. The dental implant according to claim 1, wherein at least one thread is formed on a surface of said fixture portion and said thread has depth of about 300 to about 500 $\mu$m and a pitch of about 700 to about 900 $\mu$m.

15. The dental implant according to claim 1, wherein a first thread and a second thread are alternately formed on a surface of said fixture portion.

16. The dental implant according to claim 15, wherein each of said first thread and said second thread has a depth of about 300 to about 500 $\mu$m and a pitch of about 700 to about 900 $\mu$m.

* * * * *

UNITED STATES PATENT AND TRADEMARK OFFICE
CERTIFICATE OF CORRECTION

PATENT NO. : 6,981,873 B2  Page 1 of 1
APPLICATION NO. : 10/432627
DATED : January 3, 2006
INVENTOR(S) : Y. W. Choi et al.

It is certified that error appears in the above-identified patent and that said Letters Patent is hereby corrected as shown below:

At column 11, line 42 (claim 1, line 2) of the printed patent, "in" should be --is--.

Signed and Sealed this

Third Day of October, 2006

JON W. DUDAS
*Director of the United States Patent and Trademark Office*